(12) United States Patent
Ginggen

(10) Patent No.: US 7,242,981 B2
(45) Date of Patent: Jul. 10, 2007

(54) SYSTEM AND METHOD FOR CONTROLLING AN IMPLANTABLE MEDICAL DEVICE SUBJECT TO MAGNETIC FIELD OR RADIO FREQUENCY EXPOSURE

(75) Inventor: Alec Ginggen, Neuchatel (CH)

(73) Assignee: Codman Neuro Sciences Sárl, Neuchatel (CH)

( * ) Notice: Subject to any disclaimer, the term of this patent is extended or adjusted under 35 U.S.C. 154(b) by 379 days.

(21) Appl. No.: 10/610,445

(22) Filed: Jun. 30, 2003

(65) Prior Publication Data

US 2004/0267233 A1    Dec. 30, 2004

(51) Int. Cl.
*A61N 1/00* (2006.01)
(52) U.S. Cl. .................. 607/27; 604/502; 604/891.1
(58) Field of Classification Search ............. 604/502, 604/890.1, 891.1, 892.1, 500, 506; 607/27, 607/9; 128/898
See application file for complete search history.

(56) References Cited

U.S. PATENT DOCUMENTS

| 3,311,111 | A | 3/1967 | Bowers |
| 4,091,818 | A | 5/1978 | Brownlee ............... 128/419 |
| 4,301,804 | A | 11/1981 | Thompson et al. .......... 607/30 |
| 4,494,545 | A | 1/1985 | Slocum et al. |
| 4,541,431 | A | 9/1985 | Ibrahim et al. ............ 607/30 |
| 5,197,468 | A | 3/1993 | Proctor et al. ............ 128/419 |
| 5,309,096 | A | 5/1994 | Hoegnelid ............... 324/256 |
| 5,438,990 | A | 8/1995 | Wahlstrand et al. ........ 324/260 |
| 5,584,870 | A | 12/1996 | Single et al. ............. 607/63 |

(Continued)

FOREIGN PATENT DOCUMENTS

DE    101 20 279    12/2001

(Continued)

OTHER PUBLICATIONS

Sommer, Torsten et al., "MR Imagaing and Cardiac Pacemakers: In Vitro Evaluation and in Vivo Studies in 51 Patients at 0.5T", *Radiology*, Jun. 2000, pp. 869-879.

(Continued)

*Primary Examiner*—Kevin C. Sirmons
*Assistant Examiner*—Andrew Gilbert
(74) *Attorney, Agent, or Firm*—Cheryl F. Cohen, LLC

(57) ABSTRACT

A system for controlling an implantable medical device (e.g., a drug delivery device) susceptible to malfunctioning during exposure to a magnetic field and/or Radio Frequency field (e.g., during a magnetic resonance imaging procedure) and a method for operating the same. Exposure of the implantable device to the magnetic field and/or the Radio Frequency field is detected using the sensing device. When the detected magnetic field and/or Radio Frequency field exceeds a corresponding predetermined threshold level, an input signal is generated at the microcontroller. In response to the generated input signal, the microcontroller automatically triggers (i) a safety mode enabling a predetermined safety mode operation that alters some operation, without ceasing all operation, of the implantable medical device and/or (ii) after expiration of a predetermined safety mode time interval when the at least one field being detected falls below its corresponding predetermined threshold level or a predetermined period of time elapses, a self testing mode enabling a predetermined self testing operation to verify proper operation of the implantable medical device. Preferably, both the safety and self testing modes are automatically triggered.

7 Claims, 3 Drawing Sheets

U.S. PATENT DOCUMENTS

| | | | | |
|---|---|---|---|---|
| 5,647,379 | A | | 7/1997 | Meltzer ..................... 128/897 |
| 5,649,965 | A | | 7/1997 | Pons et al. ..................... 607/2 |
| 5,662,694 | A | | 9/1997 | Lidman et al. ............... 607/60 |
| 5,694,952 | A | | 12/1997 | Lidman et al. ............. 128/899 |
| 5,697,958 | A | * | 12/1997 | Paul et al. ..................... 607/31 |
| 5,709,225 | A | | 1/1998 | Budgifvars et al. ......... 128/899 |
| 5,877,630 | A | | 3/1999 | Kraz ........................ 324/511 |
| 5,968,083 | A | | 10/1999 | Archer et al. |
| 6,198,972 | B1 | | 3/2001 | Hartlaub et al. ............... 607/63 |
| 6,505,062 | B1 | | 1/2003 | Ritter et al. ................. 600/407 |
| 6,520,006 | B2 | | 2/2003 | Burns .......................... 73/146 |
| 6,795,730 | B2 | * | 9/2004 | Connelly et al. .............. 607/9 |
| 7,082,328 | B2 | * | 7/2006 | Funke .......................... 607/9 |
| 2002/0138113 | A1 | | 9/2002 | Greatbatch et al. |
| 2003/0083570 | A1 | | 5/2003 | Cho et al. |
| 2003/0140931 | A1 | | 7/2003 | Zeijlemaker et al. |
| 2003/0144704 | A1 | | 7/2003 | Funke |
| 2003/0144705 | A1 | | 7/2003 | Funke |
| 2003/0144706 | A1 | * | 7/2003 | Funke ......................... 607/30 |
| 2004/0088012 | A1 | | 5/2004 | Kroll et al. |
| 2005/0043761 | A1 | * | 2/2005 | Connelly et al. .............. 607/2 |

FOREIGN PATENT DOCUMENTS

| | | |
|---|---|---|
| EP | 0030135 | 6/1981 |
| EP | 0530006 | 3/1993 |
| EP | 0702981 | 3/1996 |
| WO | WO 9412238 | 6/1994 |
| WO | WO 9640366 | 12/1996 |

OTHER PUBLICATIONS

Dewinder S. Bhachu and Emanuel Kanal, "Implantable Pulse Generators (Pacemakers) and Electrodes: Safety in the Magnetic Resonance Imaging Scanner Environment", *Journal of Magnetic Resonance Imaging*, vol. 12, pp. 201-204 (2000).

David R. Holmes, Jr. et al., "The Effects of magnetic Resonance Imaging on Implantable Pulse Generators", *Journal of Pacing and Clinical Electrophysiology*, vol. 9 (May-Jun. 1986) pp. 360-370.

Roger Luechinger et al., "Pacemaker Reed Switch Behavior in 0.5, 1.5, and 3.0 Telsa Magnetic Resonance Imaging Units: Are Reed Switches Always Closed in Strong Magnetic Fields?", *Journal of Pacing and Clinical Electrophysiology*, vol. 25, No. 10 (Oct. 2002) pp. 1419-1423.

Sergio L. Pinski and Richard G. Trohman, "Interference in Implanted Cardiac Devices", *Journal of Pacing and Clinical Electrophysiology*, vol. 25, No. 10 (Oct. 2002) pp. 1496-1509.

Reinhard von Roemeling et al., "MR Imaging of Patients with Implanted Drug Infusion Pumps", *JMRI*, vol. 1, No. 1, pp. 77-81 (Jan./Feb. 1991).

Beth A. Schueler et al., "MRI Compatibility and Visibility Assessment of Implantable Medical Devices", *Journal of Magnetic Resonance Imaging*, vol. 9 (1999) pp. 596-603.

Frank G. Shellock, "MR Imaging and Electronically Activated Devices", *Radiology*, vol. 219, No. 1 (Apr. 2001) pp. 294-295.

Ryan J. Uitti et al., "Magnetic Resonance Imaging and Deep Brain Stimulation", *Neurosurgery*, vol. 51, No. 6 (2002) pp. 1423-1431.

Rank G. Shellock et al., "Implantable Spinal Fusion Stimulator: Assessment of MR Safety and Artifacts", *Journal of Magnetic Resonance Imaging*, vol. 12 (2000) pp. 214-223.

Liong A. Liem and Vincent C.P.C. van Dongen, "Magnetic Resonance Imaging and Spinal Cord Stimulation Systems", *International Association for the Study of Pain* (1997) pp. 95-97.

Volker Martin Tronnier et al., "Magnetic Resonance Imaging with Implanted Neurostimulators: An In Vitro and In Vivo Study", *Neurosurgery*, vol. 44, No. 1 (Jan. 1999) pp.118-126.

Michael Niehaus & Jurgen Tebbenjohanns, "Electromagnetic interference in patients with implanted pacemakers or cardioverter-defibrillators", *Heart*, vol. 86 (2001) pp. 246-248.

Nora Goldschlager et al., "Environmental and Drug Effects on Patients with Pacemakers and Implantable Cardioverter/Defibrillators", *Arch Intern Med*, vol. 161 (Mar. 12, 2001).

Carel C. DeCock et al., "Electromagnetic Interference of an Implantable Loop Recorder by Commonly Encountered Electronic Devices", *Journal of Pacing and Clinical Electrophysiology*, vol. 23, Part I (Oct. 2000) pp. 1516-1518.

Roger Luechinger et al., "Force and Torque Effects of a 1.5-Tesla MRI Scanner on Cardiac Pacemakers and ICDs", *Journal of Pacing and Clinical Electrophysiology*, vol. 24, No. 2 (Feb. 2001) pp. 199-205.

Ole-Gunnar Anfinsen et al., "Implantable Cardioverter Defibrillator Dysfunction During and After Magnetic Resonance Imaging", *Journal of Pacing and Clinical Electrophysiology*, vol. 25, No. 9 (Sep. 2002) pp. 1400-1402.

Christian Vahlhaus et al., "Interference with Cardiac Pacemakers by Magnetic Resonance Imaging: Are There Irreversible Changes at 0.5 Tesla?", *Journal of Pacing and Clinical Electrophysiology*, vol. 24, No. 4, Part I (Apr. 2001) pp. 489-495.

Ignacio Garcia-Bolao et al., "Magnetic resonance imaging in a patient with a dual-chamber pacemaker", *Acta Cardiol*, vol. 53, No. 1 (1998) pp. 33-35.

Grank G. Shellock et al., "Cardiac Pacemakers and Implantable Cardioverter Defibrillators Are Unaffected by Operation of an Extremity MR Imaging System", *American Journal of Roentgenol*, vol. 172, No. 1 (Jan. 1999) pp. 165-170.

Stephan Achenbach et al., "Effects of magnetic resonance imaging on cardiac pacemakers and electrodes", *American Heart Journal*, vol. 134, No. 3 (1997) pp. 467-473.

Jay A. Erlebacher et al., "Effect of Magnetic Resonance Imaging on DDD Pacemakers", *American Journal of Cardiology*, vol. 57, No. 6 (Feb. 15, 1986) pp. 437-440.

David L. Hayes et al., "Effects of 1.5 Tesla Nulear Magnetic Resonance Imaging Scanner on Implanted Permanent Pacemakers", *Journal of American College of Cardiology*, vol. 10, No. 4 (Oct. 1987) pp. 782-786.

Yuzuru Sakakibara and Toshio Mitsui, "Concerns about Sources of Electromagnetic Interference in Patients with Pacemakers", *Japan Heart Journal*, vol. 40, No. 6 (Nov. 1999) pp. 737-743.

Gerhard Lauck et al., "Effects of Nuclear Magnetic Resonance Imaging on Cardiac Pacemakers", *Journal of Pacing and Clinical Electrophysiology*, vol. 18 (Aug. 1995) pp. 1549-1555.

* cited by examiner

SYSTEM AND METHOD FOR CONTROLLING AN IMPLANTABLE MEDICAL DEVICE SUBJECT TO MAGNETIC FIELD OR RADIO FREQUENCY EXPOSURE

BACKGROUND OF THE INVENTION

1. Field of the Invention

The present invention is directed to an implantable medical device and, in particular, to an implantable medical device that automatically triggers a safety mode when exposure to a static magnetic field and/or Radio Frequency (RF) field, e.g., produced by a Magnetic Resonance Imaging unit, exceeds predetermined threshold levels followed by a self testing mode once the magnetic field and/or RF field falls below the associated predetermined threshold level.

2. Description of Related Art

Magnetic Resonance Imaging (MRI) devices are widely used as a medical diagnostic tool primarily due to its non-invasive properties. MRI is based on the intrinsic property of atomic nuclei known as spin. Specifically, atomic particles in the nuclei spin about their respective axes thereby producing angular momentum. When an atom has an odd number of both protons and neutrons then an angular momentum is produced; otherwise, the angular momentum is zero when an even number of both protons and neutrons exist in the atom.

In addition, certain nuclei exhibit magnetic properties. Specifically, protons as a result of their mass, positive charge and spin produce a relatively small magnetic field (a magnetic dipole moment). When no magnetic field is present the direction of magnetic dipole moments of population of nuclei are randomly oriented. However, when subject to a relatively large external static magnetic field (e.g., along the z-axis), the proton will assume one of two possible positions, i.e., aligned substantially parallel or anti-parallel with the direction of the external magnetic field. Exposure of the proton to the external static magnetic field also causes the proton to precess (spin like a top) about their magnetic dipole moments at some frequency expressed by the following Larmor Frequency Equation:

$$\omega_0 = \gamma B_0$$

where, $\omega_0$ represents the Larmor frequency;

$\gamma$ is the gyromagnetic ratio representing the ratio between the angular momentum and the magnetic moment, wherein the gyromagnetic ratio is specific to each magnetically active nuclei; and $B_0$ is the strength of the external static magnetic field. Typically, MRI machines currently apply a static magnetic field in the range between approximately 0.7 T and 1.5 T, or even upwards of 3.0 Tesla. Even higher static magnetic fields are contemplated since the higher the field the better the resolution and definition of the image.

Generally, hydrogen nuclei spin is used in MRI procedures due to its abundant quantities in the human body. The gyromagnetic ratio for hydrogen is 42.6 MHz/T. Accordingly, the Larmor frequency for hydrogen is approximately 30 MHz for 0.7 T and approximately 64 MHz for 1.5 T.

A proton with a magnetic moment can have one of two possible energy states $I = \pm \frac{1}{2}$. When subject to an external static magnetic field, the protons align themselves substantially parallel or non-parallel (anti-parallel) to the direction of the external static magnetic field. Those protons that are non-parallel (anti-parallel) have a slightly higher energy state than those that are parallel. While in the presence of the external static magnetic field, if the protons are irradiated with a Radio Frequency (RF) signal in the x-y plane at the Larmor frequency some of the lower energy parallel protons will absorb energy from the RF wave and rotate the magnetic dipole moment to a non-parallel (anti-parallel) orientation, referred to as magnetic resonance. Those protons that have rotated to the non-parallel (anti-parallel) orientation are now in a higher energy state. After the radiation is removed, some of the non-parallel (anti-parallel) protons will rotate back to its lower energy parallel orientation (equilibrium state) and release or emit a relatively small amount of energy at the Larmor frequency to the environment as an RF wave. Detection of this relatively low level energy emission is detected by sensors and constitute the signal of interest that is used as the basis for the image.

Patient's having implanted medical devices that undergo an MRI procedure may be subject to two different types of potentially deleterious effects. This is especially noteworthy considering the fact that MRI procedures typically range in time from approximately 20 minutes to 90 minutes, or even longer. Therefore, patient's will be subject to these effects over an extended period of time.

The first effect is that resulting from the required static magnetic field at relatively high levels. While undergoing an MRI procedure, exposure to such a relatively high magnetic field may potentially cause malfunctioning or disruption in an implanted medical device of a mechanical or electromechanical component thereof that is sensitive to such relatively high static magnetic fields. For example, exposure to the magnetic field may undesirably cease or alter operation of a motor comprising magnets and coils, an electro-magnetically actuated part (e.g., a valve of a drug delivery device), an actuator, a sensor or any other component of an implantable medical device that may be sensitive to such relatively high static magnetic fields as required during MRI procedures.

Another safety precaution is the effect due to the RF field. For instance, an RF field will generate a relatively high voltage if coupled to a conductive loop. Accordingly, the RF field may cause dysfunctions at the level of electronic components (e.g., RAM, EEPROM, Flash memories, CPU function, sensors, actuators) or at the level of the system (e.g., circuit, leads).

These deleterious effects are of particular concern to those patient's having implantable medical devices (e.g., drug delivery devices, pacemakers, defibrillators or stimulators) employing components (e.g., motors, valves, actuators, sensors, integrated circuits, memory chips or solid state sensors) that may be sensitive to the relatively high magnetic fields and/or RF fields produced during the MRI procedure. These adverse effects on implantable medical devices produced during MRI procedures has led the medical industry to recommend that patients having such devices forego MRI as a diagnostic imaging tool. In the event that a patient still chooses to undergo an MRI then the manufacturers of the electronically operated implantable medical devices typically advise the patient to have the implant parameters verified and reset after the procedure generally using an external reading unit that communicates by telemetry with the implant device. This verification or checking of the operation of the implantable medical device is impractical in that it does not alter or correct the potentially inaccurate operation of the device during the procedure and requires external reading instrumentation particular to the implant device by specially trained medical personnel to be present immediately following the medical procedure to verify the accuracy of its operation.

Recently research and development has focused on finding a solution for detecting when electronic implantable devices are subject to adverse interference from electromagnetic radiation (Radio Frequency radiation). U.S. Pat. No. 6,198,972 discloses an apparatus for limiting unwanted current induced by a significant level of an external signal such as a time-alternating electromagnetic field in a conductive loop used to deliver electrical stimulation to electrically excitable tissue. Such electrical stimulation for instance may be applied to brain tissue to reduce or suppress tremors, peripheral nerve tissue to promote blood circulation and for pain management. The electrodes are electrically connected by a conductive lead wire to an implantable pulse generator. A switch is operatively connected within the conductive loop between the two devices and is controlled by control circuits. The switch is turned on when the level of detected electromagnetic radiation is less than or equal to a predetermined threshold thereby closing the conductive loop and allowing the electrical stimulation to excite the tissue, whereas the switch is turned off and the conductive loop is opened when the detected electromagnetic field exceeds the specified threshold. Since the switch is turned off and the conductive loop is opened when the external electromagnetic field exceeds the specified threshold all operations or actions by the medical device cease during this period of adverse electromagnetic exposure until the switch is once again turned on and the conductive loop is closed when exposure ceases. For instance, no electrical stimulus can be applied during this time as a result of the cutoff of connectivity to the pulse generator. This patented device would therefore not be suitable for a medical device that must continue some type of operation or functionality during this interval of exposure. Furthermore, no testing is disclosed to verify that the stimulating electrodes are working properly once exposure has ceased and the switch changes to a closed state.

Another device is described in U.S. Pat. No. 5,877,630 in which the field strength and amplitude modulation of the electromagnetic radiation is detected. So long as the combined field strength and amplitude modulation of the detected electromagnetic radiation (Radio Frequency radiation) exceeds a predetermined threshold level, the operation of the electronic device is continuously tested. Specifically, a series of testing pulses are continuously generated and sent to the CPU of the electronic device so long as the combined signal of field strength and amplitude modulation of the detected electromagnetic radiation exceeds the predetermined threshold. A response from the CPU to each pulse is expected within a predetermined time interval as confirmation that the medical device is operating properly. Each time the CPU responds to a testing pulse a countdown timer is reset. The timer counts down with each pulse signal that is not responded to by the CPU until the timer reaches zero whereupon an alarm may be sounded. Therefore, this device does not assume that the medical device will not operate properly simply because the device is subject to electromagnetic radiation that exceeds a predetermined threshold level. Instead, a second level of criteria is applied when the threshold level is exceeded, that is, testing the operation of the CPU in responding back to continuously generated test pulses. Only if both criteria are met, i.e., the radiation exceeds a threshold level and no response is received to the generated test pulse within a predetermined time period, is the medical device classified as working improperly. This patented device is inefficient in its expenditure of energy to generate the testing pulses during the entire time interval that the medical device is subject to electromagnetic radiation exceeding the predetermined threshold. In addition, the device fails to take into consideration the situation in which the CPU responds to the test pulse but nevertheless operation of the medical device has been altered or disrupted in other ways (e.g., timing frequency has been altered or data stored in memory has been corrupted, altered or erased) due to interference from exposure to the electromagnetic radiation. Yet another disadvantage is that no verification of operation of the medical device is conducted after its exposure to the electromagnetic radiation ceases, testing occurs only while the device is subject to the electromagnetic radiation exceeding the predetermined threshold level.

It is therefore desirable to develop an implantable medical device that automatically activates at least one of, preferably both, a safety mode triggering some modified or altered operation of some part of the implantable medical device when exposed to a magnetic field and/or RF field that exceeds acceptable predetermined thresholds. When exposure to the static magnetic field and/or RF field falls below the predetermined threshold, thereafter automatically switching from a safety mode to a self testing mode so as to verify that the medical device is operating properly.

SUMMARY OF THE INVENTION

The present invention solves the aforementioned problems associated with conventional implantable medical devices. In particular, the invention relates to a method for operating a system for controlling an implantable drug delivery device susceptible to malfunctioning during exposure to a magnetic field and/or a Radio Frequency field. The system includes a microcontroller and a sensing device for detecting the magnetic field and/or the Radio Frequency field. Exposure of the implantable device to the magnetic field and/or the Radio Frequency field generated during the magnetic resonance imaging procedure is detected using the sensing device. When the detected magnetic field and/or Radio Frequency field exceeds a corresponding predetermined threshold level, generating an input signal (e.g. interrupt signal) at the microcontroller. After generating the input signal, the microcontroller automatically triggers (i) a safety mode enabling a predetermined safety mode operation that alters some operation, without ceasing all operation, of the implantable drug delivery device; and/or (ii) after expiration of a predetermined safety mode time interval when the at least one field being detected falls below its corresponding predetermined threshold level or a predetermined period of time elapses, a self testing mode enabling a predetermined self testing operation to verify proper operation of the implantable drug delivery device.

In addition, the present invention is also directed to a system for controlling an implantable drug delivery device susceptible to malfunctioning during exposure to a magnetic field and/or a Radio Frequency field. The system includes a sensing device for detecting exposure of the implantable device to the magnetic field and/or the Radio Frequency field generated during the magnetic resonance imaging procedure. A microcontroller is electrically connected to the sensing device. The microcontroller receives an input signal when the at least one field being detected exceeds a corresponding predetermined threshold level. After receiving the input signal, the microcontroller automatically triggers at least one of (i) a safety mode enabling a predetermined safety mode operation that alters some operation, without ceasing all operation, of the implantable drug delivery device; or (ii) after expiration of a predetermined safety mode time interval when the at least one field being detected falls below its corresponding predetermined threshold level or a predetermined period of time elapses, a self testing mode enabling a predetermined self testing operation to verify proper operation of the implantable drug delivery device.

In yet another embodiment, the invention relates to a system and method for operating a system for controlling an implantable medical device susceptible to malfunctioning during exposure to at least one of a magnetic field or a Radio Frequency field. Initially, exposure of the implantable device to the magnetic field and/or the Radio Frequency field using a sensing device. When the at least one field being detected exceeds a corresponding predetermined threshold level an input signal is generated at the microcontroller. In turn, the microcontroller automatically triggers (i) a safety mode enabling a predetermined safety mode operation that alters some operation, without ceasing all operation, of the implantable medical device; and (ii) after expiration of a predetermined safety mode time interval when the at least one field being detected falls below its corresponding predetermined threshold level or a predetermined period of time elapses, a self testing mode enabling a predetermined self testing operation to verify proper operation of the implantable medical device.

BRIEF DESCRIPTION OF THE DRAWING

The foregoing and other features of the present invention will be more readily apparent from the following detailed description and drawings of illustrative embodiments of the invention wherein like reference numbers refer to similar elements throughout the several views and in which.

DETAILED DESCRIPTION OF THE INVENTION

Figure 1:
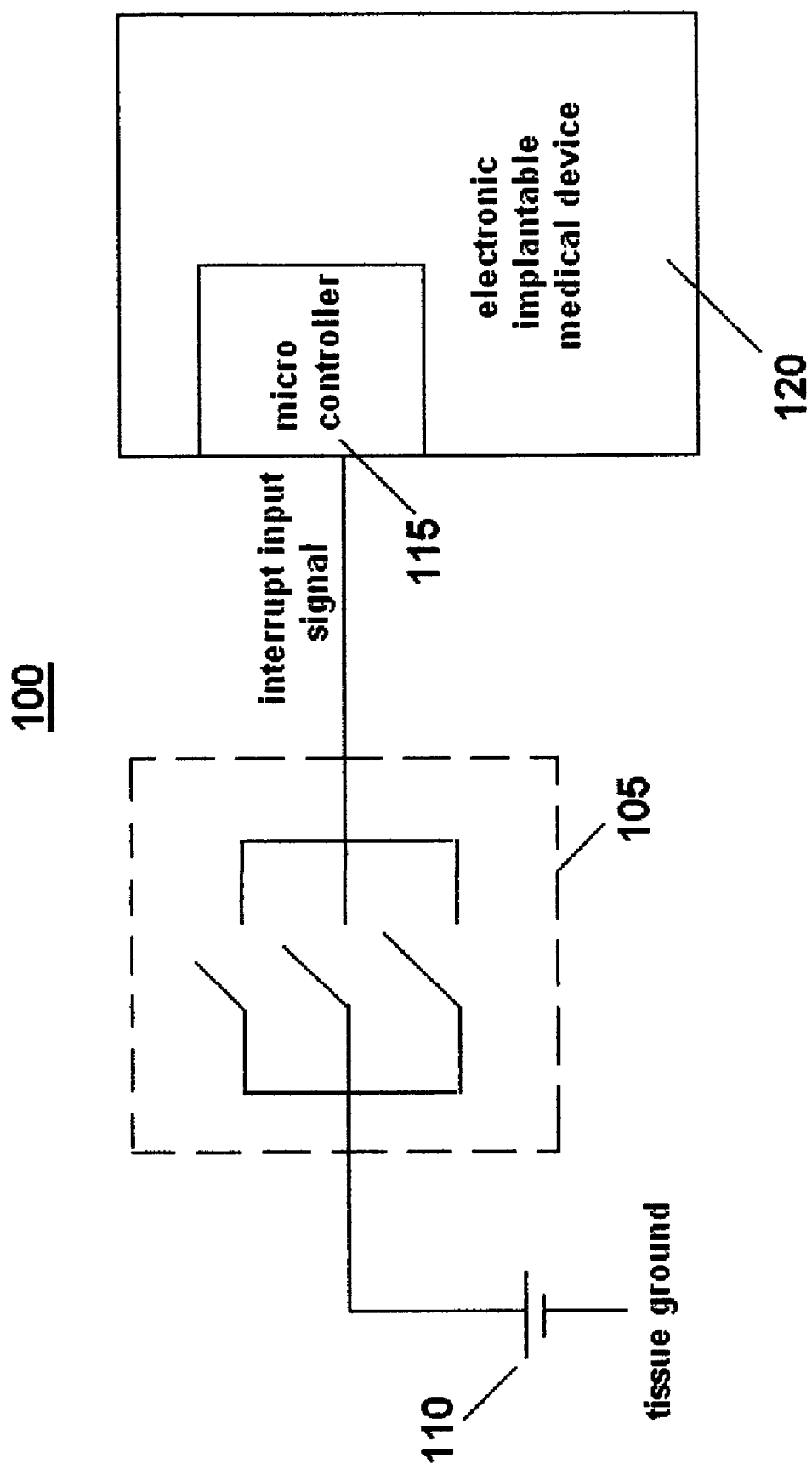
FIG. 1 is an exemplary schematic circuit diagram of a first embodiment of an implantable medical device with magnetic field detection in accordance with the present invention using three Reed switches arranged substantially orthogonal relative to one another.

An exemplary schematic circuit diagram of a first embodiment of a system 100 for controlling an implantable medical device based on magnetic field exposure in accordance with the present invention is shown in FIG. 1. Although not shown, the system 100 is preferably encased or enclosed in a housing. System 100 includes an electronic implantable medical device 120, for example, a drug delivery device, a pacemaker, a defibrillator, a cochlear implant or a stimulator, that employs an electronic component (e.g., integrated circuits, memory chips or solid state sensors) which may be sensitive to or whose operation may be altered/disrupted in the presence of high intensity magnetic fields, typically between approximately 0.2 T and 3.0 T, generated by an MRI unit. A magnetic field sensor 105 is connected in parallel to a power source (e.g., a battery) 110 and to a microcontroller 115 (e.g., microprocessor) that electronically controls the implantable medical device 120.

In the embodiment shown in FIG. 1, the magnetic field sensor 105 is configured as three Reed switches arranged substantially orthogonal to one another so as to detect static magnetic fields in three spatial directions (e.g., corresponding to the three X, Y and Z axes of three dimensional Cartesian coordinates). Any number of one or more Reed switches may be used to detect the magnetic fields. As the number of magnetic field sensors employed is reduced the sensitivity to magnetic fields in all spatial directions (360 degrees) about the patient decreases. Reed switches or some other type of passive magnetic field detection device is preferred in that it only consumes energy when subject to magnetic field intensities that exceed a predetermined magnetic field sensitivity threshold.

Each Reed switch has an associated sensitivity representing the magnetic field required to activate that switch. The sensitivity of each of the three Reed switches may be independently selected so that the sensitivity of each is the same or different. MRI units produce magnetic fields typically in the range between approximately 0.7 T and 3.0 T. Accordingly, in a preferred embodiment, the sensitivity of the Reed switch is selected at greater than or equal to approximately the minimum magnetic field produced by the MRI unit, e.g., approximately 0.7 T. Experimental testing may determine that particular electronic implantable medical devices are able to operate properly at the lower end of the range of magnetic field levels produced by the MRI. In that case, a higher sensitivity of the Reed switch substantially equal to the magnetic field level at which operation of the implantable medical device is disrupted or altered may be selected. Accordingly, the sensitivity threshold of each magnetic sensor may be selected, as desired. It is most likely that extensive testing for each particular electronic implantable medical device and its inoperativeness or malfunctioning due to interference from exposure to certain levels of magnetic field radiation is not known. Therefore, to be certain the sensitivity threshold is preferably not less than the minimum magnetic field intensity and/or frequency a patient is subject to while undergoing diagnostic MRI imaging for a particular machine.

For purposes of illustration only, the operation of the detection mechanism having 3 Reed switches arranged substantially orthogonal relative to each other and all having the same sensitivity will be described. In operation, while the patient is not undergoing MRI testing, exposure of the electronic implantable medical device to a magnetic field should not exceed the sensitivity of any of the Reed switches and so the switches will remain open thereby maintaining normal operation of the electronic implantable medical device 120 by the microcontroller 115. If the magnetic field detected by any one or more of the Reed switches exceeds its associated sensitivity then that switch will be closed generating an input signal (e.g., an interrupt signal) at the microcontroller 115. Interruption of the microcontroller, in turn, automatically triggers a safety mode comprising one or more predetermined operations associated with the implantable medical device. During the safety mode the microcontroller 115 triggers modified or altered operation of the implantable medical device, without ceasing altogether operation of the implantable medical device. For example, the safety mode may initiate any one or more of the following operations: (i) cease or alter operation of the electronic implantable medical device, (ii) duplicate all data and/or save all data to memory (e.g., in a RAM or EEPROM memory); (iii) calculate memory checksums to be verified during the self testing mode, and (vi) store data detected by the sensing device. In addition, the safety mode may also short circuit the transmitter/receiver (e.g., antenna) of the electronic implantable medical device to de-tune it so as to avoid generation of high tension at that level of high frequency emission. In the case of a drug delivery electronic implantable medical device, the predetermined safety mode operations may include ceasing all drug delivery operations to avoid drug overdose. Alternatively, the delivery of drugs may be set to revert back to a default rate or level of delivery stored in a non-volatile memory at the time of implantation in the patient. These safety mode operations are sustained during the entire MRI imaging procedure referred to as the safety mode time interval. The safety mode time interval may be measured by the passing of a predetermined period of time (e.g., using a timer, counter or other timing mechanism) or until the detected magnetic field intensity falls below a predetermined threshold level (e.g., all of the Reed switches open as a result of the reduction in the detected magnetic field intensity below the sensitivity of the corresponding switches).

At the end of the safety mode time interval a self test mode is automatically triggered in the microcontroller code, while continuing or maintaining the safety mode operations, to verify that the implant medical device is operating properly. Thus, during this self testing mode, the predetermined safety mode operations remain in effect simultaneously while the self testing operations are being performed. In particular, the self test mode initiates one or more of the following predetermined operations: checking or verifying of memory contents (e.g., compare memory checksums before and after triggering of safety mode), testing memory operation (read/write test of memory device), and verifying the operation of components of the implantable medical device (e.g., battery level, crystal frequency, oscillator frequencies, input range of sensing device, communication ports of microcontroller). If the memory content and magnetic field detection sensor verifications do not detect an error then the predetermined safety mode operation is disabled and normal operations of the electronic implantable medical device is restored. Otherwise, an alarm or other device is preferably triggered alerting the patient and medical personnel to check and, if necessary, correct the operation of the implantable medical device via telemetry. In the latter case in which an error is detected, the predetermined safety mode operations continue until disabled by telemetry after the detected error has been corrected.

Figure 2:
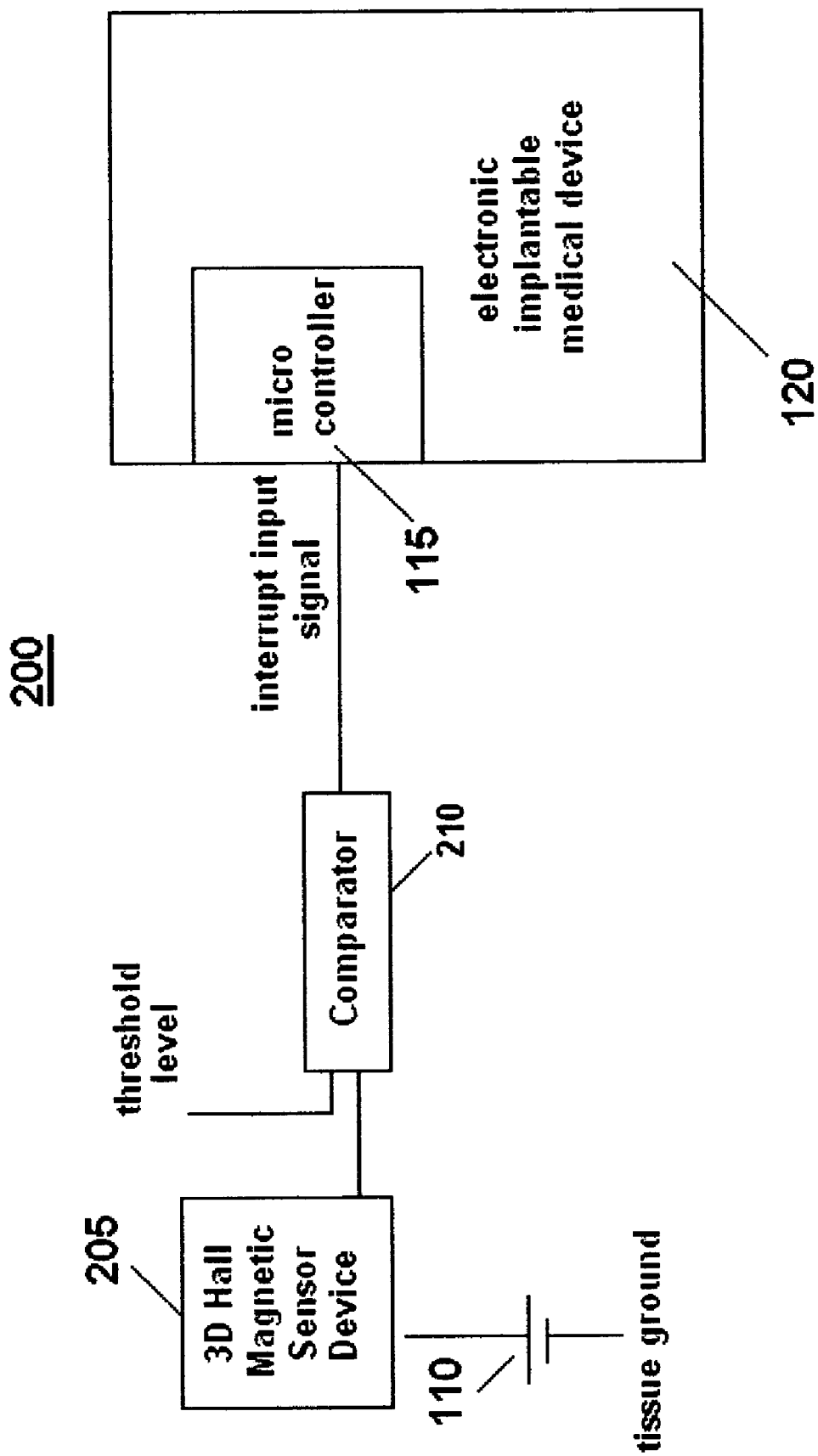
FIG. 2 is an exemplary schematic circuit diagram of a second embodiment of an implantable medical device with magnetic field detection in accordance with the present invention using a 3D Hall Magnetic sensor.

The magnetic field detection device in FIG. 1 employs passive magnetic field sensors, e.g., Reed switches. Alternatively, active magnetic fields sensors may be used as shown in FIG. 2. The same elements shown in FIGS. 1 and 2 are referred to by the same reference element numbers. Only those devices that differ between the two embodiments will be described further. Specifically, the embodiment shown in FIG. 2 differs from that in FIG. 1 in that a 3D Hall Magnetic Sensor Device 205, for example, as manufactured by Sentron Ag in Switzerland, is employed instead of the Reed switches. The Magnetic Sensor Device 205 shown in FIG. 2 preferably include 3 Hall Magnetic Sensor, however, any number of one or more Hall Magnetic Sensors are contemplated and within the intended scope of the invention. In addition, other active magnetic field sensors may be used instead of the Hall magnetic sensors. The Magnetic Sensor Device 205 generates an analog output signal that is connected to a comparator 210 that also receives as input an appropriate reference magnetic field threshold level. If the signal intensity of the magnetic field exceeds the threshold level, the comparator 210 toggles and generates an input signal (e.g., interrupt signal) at the microcontroller 115 thereby triggering the safety mode. In all other respects the operation of the system in accordance with this second embodiment is similar to that previously described with respect to the first embodiment.

Figure 3:
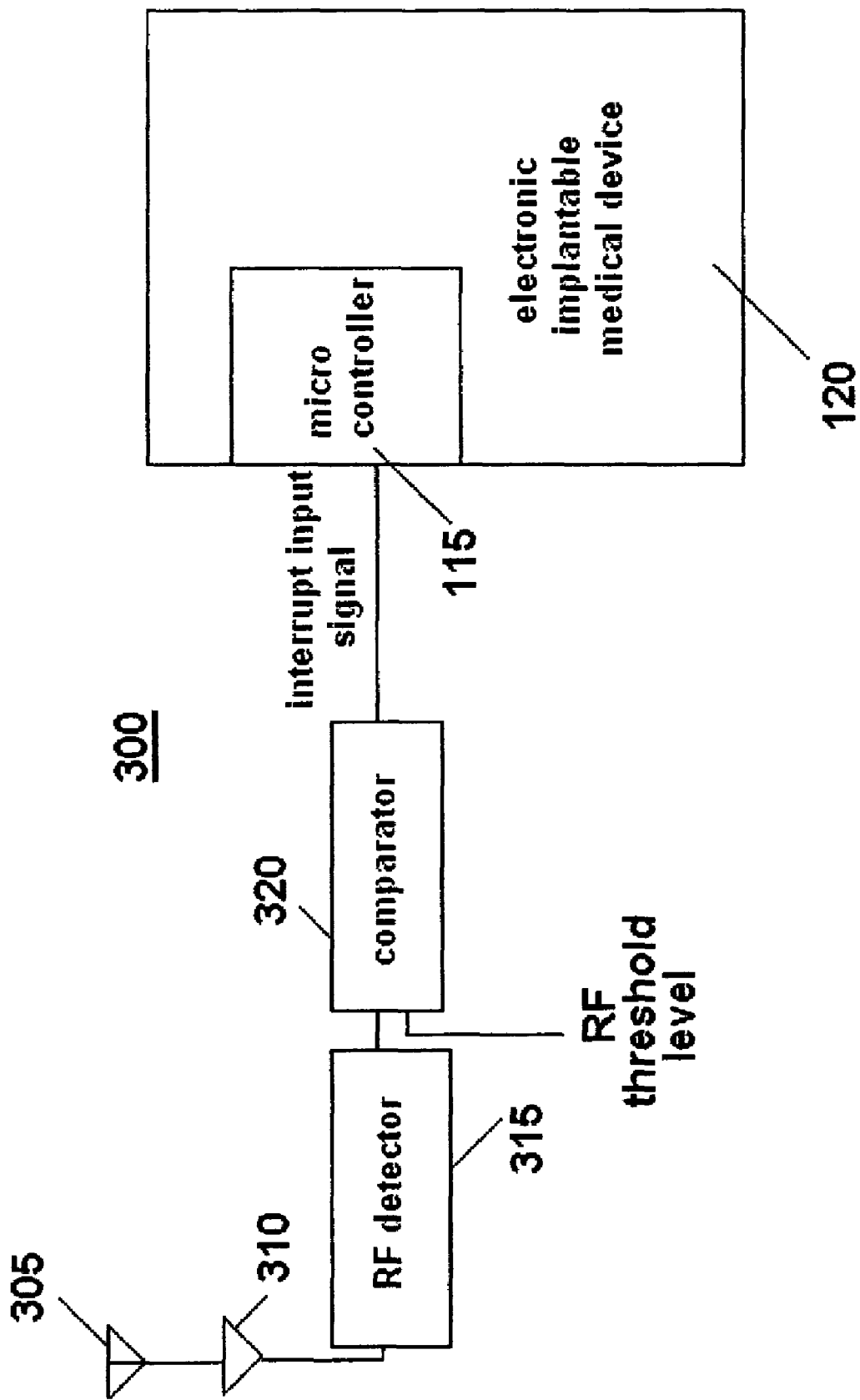
FIG. 3 is an exemplary schematic circuit diagram of a third embodiment of an implantable medical device with RF detection.

In the previously described first and second embodiments the system include magnetic field sensors for detecting that the patient is undergoing an MRI procedure when the implantable medical device is exposed to a magnetic field that exceeds a corresponding predetermined magnetic field threshold level. In an alternative embodiment shown in FIG. 3, instead of using a sensing device that detects a magnetic field, the implantable medical device includes a sensing device for detecting that the patient is undergoing an MRI procedure by sensing when the RF field exceeds a predetermined RF threshold level. In this embodiment the RF signal is received by the antenna 305 and then amplified by an amplifier 310. The amplified signal is then received as input by an RF detector 315. Any conventional RF detection means may be used. Output from the RF detector 315 is fed as input into a comparator 320 that also receives as input a RF threshold level. When the detected RF field exceeds the RF threshold level the comparator 320 toggles and generates an input signal (e.g., interrupt signal) at the microcontroller 115 thereby triggering the safety mode. In all other respects, the operation of the system 300 is similar to that previously described with respect to systems 100 and 200 in the first and second embodiments, respectively, and thus need not be described in detail further. Alternative means for detecting the RF field may be used, as desired.

It is also contemplated and within the intended scope of the present invention to employ a sensing device that detects both a magnetic field and a RF field thereby monitoring whether a patient is undergoing an MRI procedure when both the detected magnetic field and the detected RF field exceed their corresponding predetermined threshold levels. In addition, the description above is directed to the preferred embodiment in which the microcontroller of the implantable medical device triggers a safety mode followed by a self testing mode. This embodiment is preferred in that it maximizes safety precautions against possible malfunctioning or disruption of the implantable medical device. The invention, however, may be readily modified so that the microcontroller triggers either: (i) the safety mode when the detected magnetic and/or RF field exceeds its corresponding predetermined threshold to alter or modify the operations of the implantable medical device while undergoing MRI procedures; or (ii) the self testing mode, after the passage of a predetermined safety mode time interval to verify the operation of the implantable medical device, but not both.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. A method for operating a system for controlling an implantable drug delivery device susceptible to malfunctioning during exposure to at least one of a magnetic field or a Radio Frequency field, the method comprising the steps of:

detecting exposure of the implantable device to the at least one of the magnetic field or the Radio Frequency field using a sensing device;

when the at least one field being detected exceeds a corresponding predetermined threshold level, generating an input signal at a microcontroller;

automatically triggering, in response to the generated input signal, a safety mode enabling a predetermined safety mode operation that comprises: (i) duplicating all data, (ii) saving all data to a memory, (iii) short circuiting a transmitter/receiver of the implantable drug delivery device, (iv) reverting to a default operation of the implantable drug delivery device stored in a non-volatile memory at the time of implantation, (v) calculating memory checksums to be verified during the self testing mode, (vi) store data detected by the sensing device, and (vii) ceasing delivery of drugs.

2. The method in accordance with claim 1, wherein the sensing device comprises a plurality of Reed switches or a plurality of Hall Magnetic Sensors.

3. The method in accordance with claim 1, further comprising the step of:

automatically triggering, in response to the generated input signal, after expiration of a predetermined safety mode time interval when the at least one field being detected falls below its corresponding predetermined threshold level or a predetermined period of time elapses, a self testing mode enabling a predetermined self testing operation to verify proper operation of the implantable medical device.

4. The method in accordance with claim 3, wherein the safety mode is automatically triggered followed by the self testing mode, the predetermined safety mode operation continuing simultaneously with the predetermined self testing mode operation.

5. The method in accordance with claim 3 wherein the predetermined self testing mode operation comprises at least one of: (i) verifying of memory contents and (ii) testing operation of memory device of the implantable medical device.

6. The method in accordance with claim 4, further comprising, if no error in operation is detected during the self testing mode, disabling the predetermined safety mode operation.

7. The method in accordance with claim 4, further comprising the steps of:

when an error in operation is detected during the self testing mode, indicating that the error has been detected; and disabling the predetermined safety mode operation when the error in operation has been corrected.

* * * * *